(12) United States Patent
Mao et al.

(10) Patent No.: US 8,481,741 B2
(45) Date of Patent: Jul. 9, 2013

(54) PREPARATION METHODS OF 6 SUBSTITUTED AMINO-3 CYANOQUINOLINE COMPOUNDS AND THE INTERMEDIATES THEREOF

(75) Inventors: Yongjun Mao, Shanghai (CN); Jianfeng Li, Shanghai (CN); Jin Zheng, Shanghai (CN); Zheng Liu, Shanghai (CN); Kai Xie, Shanghai (CN); Haihong Li, Shanghai (CN); Jing Shi, Shanghai (CN); Ye Li, Shanghai (CN); Jingshan Shen, Shanghai (CN)

(73) Assignees: Topharman Shanghai Co., Ltd., Pudong, Shanghai (CN); Shanghai Institute of Materia Medica, Chinese Academy of Sciences, Zhang Jiang, Pudong (CN)

( * ) Notice: Subject to any disclaimer, the term of this patent is extended or adjusted under 35 U.S.C. 154(b) by 110 days.

(21) Appl. No.: 13/125,721

(22) PCT Filed: Oct. 23, 2009

(86) PCT No.: PCT/CN2009/001176
§ 371 (c)(1),
(2), (4) Date: Jun. 16, 2011

(87) PCT Pub. No.: WO2010/045785
PCT Pub. Date: Apr. 29, 2010

(65) Prior Publication Data
US 2011/0263860 A1   Oct. 27, 2011

(30) Foreign Application Priority Data
Oct. 24, 2008   (CN) .......................... 2008 1 0201758

(51) Int. Cl.
*C07D 215/38* (2006.01)
(52) U.S. Cl.
USPC ....................................................... 546/155
(58) Field of Classification Search
USPC ....................................................... 546/155
See application file for complete search history.

(56) References Cited

U.S. PATENT DOCUMENTS
5,808,016 A    9/1998  Kunde
6,143,208 A   11/2000  Buchecker et al.
6,933,388 B2 * 8/2005  Duncan et al. ............... 546/155

FOREIGN PATENT DOCUMENTS
CN    101012225         8/2007
CN    101012225 A  *    8/2007
WO    03/093241        11/2003
WO    2005/034955       4/2005
WO    2006/127207  *   11/2006

OTHER PUBLICATIONS

El-Hamouly, Eur J med Chem, vol. 28, pp. 913-916, 1993.*

International Search Report for PCT/CN2009/001176, dated Jan. 28, 2010.
Simonsen et al., "Nitration of isomeric acetylaminomethoxybenzoic acids", *Journal of the Chemical Society Transactions*, 1917, 111, pp. 220-236.
Nomoto et al., "Studies on cardiotonic agents I, Synthesis of some quinazoline derivaties", *Chemical & Pharmaceutical Bulletin*, 1990, vol. 38, No. 6, pp. 1591-1595.
Li et al., "Synthesis of 4-chloro-7-methoxy-6-pivalam idoquinazoline", *Hauxue Yanju Yu Yingyong*, 2008, vol. 20, No. 9, pp. 1216-1219.
Chen et al., "The synthesis of nitroanilline monomers and polymers as non-linear optical ferroelectric liquid crystals", *Liquid Crystals*, 1996, vol. 20, No. 2, pp. 125-138.
Ei-Hamouly et al., "Preparation and antitumor activity of an N-methylcarbarnate derivative of amsacrine", *European Journal of Medicinal Chemistry*, 1993, vol. 28, No. 12, pp. 913-916.
Nomoto et al., "Studies on cardiotonic agents I, Synthesis of some quinazoline derivatives", *Chemical & Pharmaceutical Bulletin*, 1990, vol. 38, No. 6, pp. 1591-1595.

(Continued)

*Primary Examiner* — D M Seaman
(74) *Attorney, Agent, or Firm* — Nixon & Vanderhye P.C.

(57) ABSTRACT

The present invention relates to a method for preparing 6-substituted amino-3-cyanoquinoline compounds (compound A for short) and the intermediates thereof, more particularly, to a compound of the following formula (I), the preparation method thereof, the intermediates thereof and use thereof for preparing the compound A. The compound of the formula (I) is cyclized in the presence of an alkali to give a compound of formula A, wherein W is OH; or the compound of the formula (I) is cyclized in the presence of an alkali, and then chlorinated to give a compound of the formula A, wherein W is Cl. Compared with the known methods in the literature, the method for preparing the compound A from the compound of formula (I) according to the present invention can avoid using high-temperature condition and high boiling point solvents, and is safe and environment-friendly, mild in reaction condition, easy in operation with a high yield and high product purity.

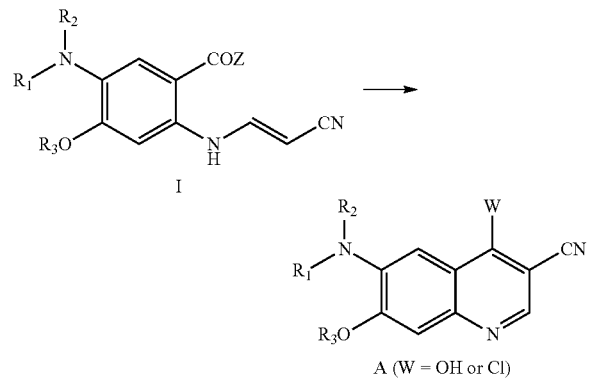

14 Claims, No Drawings

OTHER PUBLICATIONS

Li et al., "Synthesis of 4-chloro-7-methoxy-6-pivalamidoquinazoline", *Huaxue Yanju Yu Yingyong*, 2008, vol. 20, No. 9, pp. 1216-1219.

Chen et al., "The synthesis of nitroaniline monomers and polymers as non-linear optical ferroelectric liquid crystals", *Liquid Crystals*, 1996, vol. 20, No. 2, pp. 125-138.

Rene et al., "A One Pot Synthesis of β-Cyanoenamines", *Synthesis*, 1986, 5, pp, 419-420.

Wissner et al., "Synthesis and Structure-Activity Relationships of 6,7-Disubstituted 4-Anilinoquinoline-3-carbonitriles. The Design of and Orally Active, Irreversible Inhibitor of the Tyrosine Kinase Activity of the Epidermal Growth Factor Receptor (EGFR) and the Human Epidermal Growth Factor Receptor-2 (HER-2)", *J. Med. Chem.*, 2003, 46, pp. 49-63.

\* cited by examiner

PREPARATION METHODS OF 6 SUBSTITUTED AMINO-3 CYANOQUINOLINE COMPOUNDS AND THE INTERMEDIATES THEREOF

This application is the U.S. national phase of International Application No. PCT/CN2009/001176 filed 23 Oct. 2009 which designated the U.S. and claims priority to CN 200810201758.6 filed 24 Oct. 2008, the entire contents of each of which are hereby incorporated by reference.

TECHNICAL FIELD

The present invention relates to methods for preparing 6-substituted amino-3-cyanoquinoline compounds (hereafter referred to as compounds A) and the intermediates thereof, and to the methods for preparing the intermediates. More particularly, the present invention relates to compounds of formula (I) as shown hereinafter and the preparation methods thereof, the intermediates during the preparation and the use thereof for preparing the compounds A.

BACKGROUND ART 6-substituted amino-3-cyanoquinoline compounds (compounds of formula A) are important pharmaceutical intermediates. They also are key intermediates for preparing 3,4-disubstituted quinoline compounds.

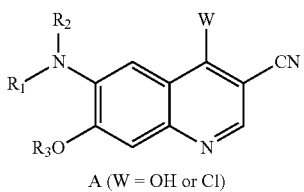

A (W = OH or Cl)

For example, 6-substituted amino-4-hydroxy-3-cyanoquinoline (compounds A1) and 6-substituted amino-4-chloro-3-cyanoquinoline (compounds A2) are important intermediates for preparing compound HKI-272. The compound HKI-272 is an irreversible small molecular tyrosine kinase inhibitor (Journal of Medicinal Chemistry, 46(1):49-63) useful for treating Colorectal cancer, Breast cancer, non-small-cell lung cancer, and has entered into clinic trial phase, being most likely to become a new anticancer drug with a promising market. Therefore, it is of great practical value to optimize the synthetic process of compounds A.

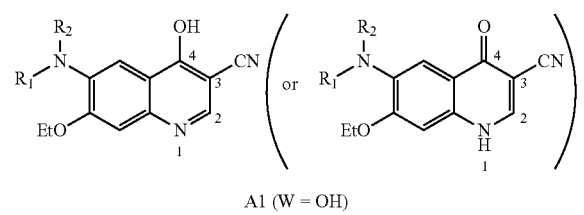

A1 (W = OH)

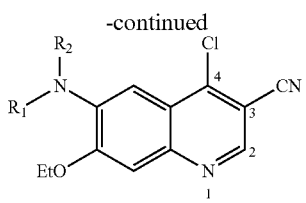

A2 (W = Cl)

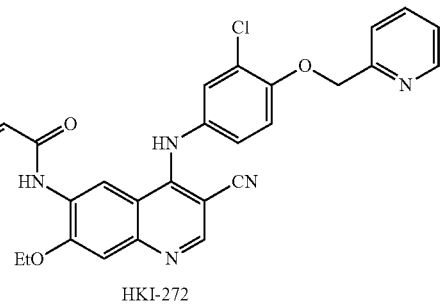

HKI-272

The key step to prepare compounds A is the formation of a quinoline ring, which usually requires a high temperature condition. For example, compound B is heated at 240-260° C. for 10-20 h in high boiling point solvents (scheme 1) (WO03093241, US2005065181, CN101012225). The reaction condition is much rigorous, and the high temperature may cause decomposition of the product, increase of by-products and low purity of product. Thus, this step has a low yield of only about 40%. Furthermore, the high boiling point solvents such as Dowtherm A are volatilized at the high temperature, which has inevitably an adverse affect on the work environment and the health of the operator, and pollution of the environment. Therefore, there is an urgent need to develop an improvement preparation method possessing mild reactive condition, high yield, little pollution to the environment, and being suitable for industry production.

Scheme 1

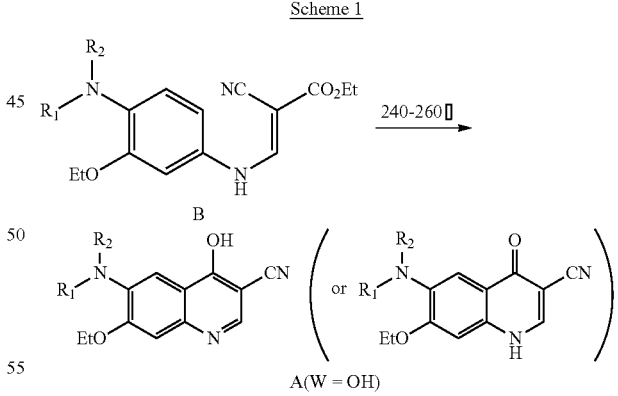

A(W = OH)

DESCRIPTION OF THE INVENTION

The present inventors have been devoted to develop a preparation method of compound A, which is mild in reactive condition, simple in operation, high in yield, low in cost, safe and environment-friendly, and suitable for large-scale industry production. Thus compounds of the following formula (I) are invented, and compounds A are synthesized simply and safely from the compounds of the following formula (I).

Therefore, an object of the present invention is to provide compounds of the following formula (I). Another object of the present invention is to provide preparation methods of the compound of the formula (I). Still another object of the present invention is to provide intermediates for producing the compounds of the formula (I). A further object of the present invention is to provide the use of the compounds of the formula (I) for producing the compounds A.

According to one object of the present invention, there is provided compounds of the following formula (I):

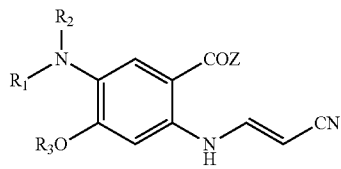

Wherein, Z is OR or $NH_2$;

R is hydrogen, C1-C10 linear or branched alkyl, C2-C5 alkenyl, aryl, or C1-C5 alkyl substituted with aryl;

$R_1$ and $R_2$ are each independently hydrogen, formyl, C1-C10 alkyl, C2-C10 alkenyl, aryl, C1-C10 alkyl substituted with aryl, C1-C10 alkylcarbonyl, arylcarbonyl

C1-C10 alkylcarbonyl substituted with aryl, C1-C10 alkoxycarbonyl, or C1-C10 alkoxycarbonyl substituted with aryl;

$R_3$ is C1-C10 alkyl, C2-C10 alkenyl, or aryl, wherein the alkyl is optionally substituted with halogen, alkoxy, aryl or a heterocyclic group having 1-2 heteroatoms selected from the group consisting of O and N, wherein the heterocyclic group is optionally substituted with C1-C10 alkyl or C1-C10 alkoxy;

wherein the aryl is phenyl, or an aromatic heterocyclic group such as thiazolyl, pyrazolyl, pyridyl, imidazolyl, and the like.

It is defined in the present application as follows: a C1-C10 alkylcarbonyl means that the alkyl group therein may be an alkyl group having 1-10 carbon atoms; and a C1-C10 alkoxycarbonyl means that the alkyl group therein may be a alkyl group having 1-10 carbon atoms. The other similar groups should be understood in the similar manner as above.

In a preferred embodiment of the present invention, it is preferable in the compound of the formula (I) that, Z is OR or $NH_2$, and more preferably is OR;

R is C1-C4 linear or branched alkyl, benzyl or phenyl, and more preferably methyl, ethyl or phenyl;

$R_1$ is hydrogen, formyl, C1-C4 alkylcarbonyl or C1-C4 alkyl, and more preferably hydrogen, formyl, acetyl, methyl or ethyl;

$R_2$ is hydrogen, formyl, C1-C4 alkylcarbonyl or C1-C4 alkyl, and more preferably hydrogen, formyl, acetyl, methyl or ethyl;

$R_3$ is C1-C5 alkyl, phenyl,

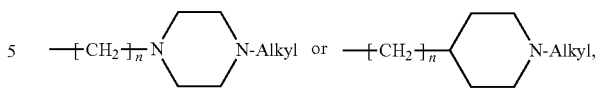

in which n is an integer from 1 to 5, Alkyl is C1-C5 alkyl, and more preferably, $R_3$ is methyl, ethyl,

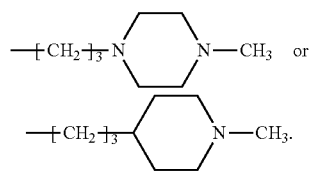

The compound of the formula (I) is most preferably selected from the following products:

Methyl 2-[(2-cyanovinyl)amino]-4-ethoxy-5-acetylamidobenzoate;

Ethyl 2-[(2-cyanovinyl)amino]-4-ethoxy-5-acetylamidobenzoate; or

Phenyl 2-[(2-cyanovinyl)amino]-4-ethoxy-5-acetylamidobenzoate.

According to another object of the present invention, there is provided a preparation method of the compound of the formula (I), comprising:

Condensing the compound of the formula (II) or acid addition salt thereof with cyanoacetaldehyde to give the compound of the formula (I);

or, treating the compound of the formula (II) or acid addition salt thereof with the compound of the formula (IV) or (V), precursors of cyanoacetaldehyde, to give the compound of the formula (I);

or, in a one-pot process, compound (VI) is first treated in a certain reaction condition or in the presence of catalyst to give cyanoacetaldehyde, which, without separation, is condensed directly with the compound of the formula (II) or acid addition salt thereof to give the compound of the formula (I);

wherein, the reaction scheme is as follows:

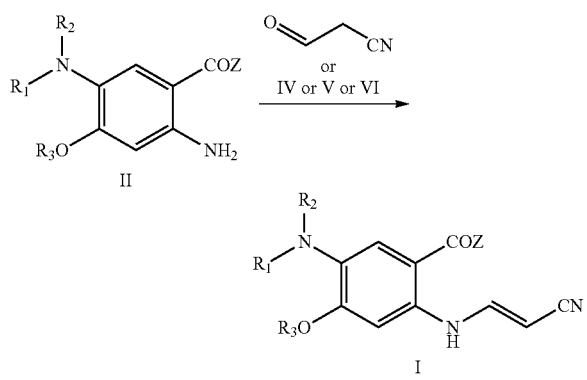

wherein, Z, $R_1$, $R_2$ and $R_3$ are defined the same as the above, the acid addition salt of the compound of the formula (II) is an inorganic acid salt thereof, such as hydrochloride, sulphate or phosphate and the like, or an organic acid salt thereof, such as methylsulfonate, p-toluenesulfonate and the like, but the present invention is not limited thereto.

The compound (IV) or (V), precursor of cyanoacetaldehyde, has a structure as follows:

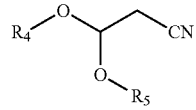

(IV)

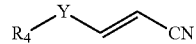

(V)

wherein, Y is O or N—$R_5$; $R_4$ and $R_5$ each independently are hydrogen or C1-C5 alkyl, or $R_4$ and $R_5$ may together form a 5-7-membered ring, which may contain one or more heteroatoms selected from the group consisting of O, N, S and the like. Preferably, the compound (IV) is 2-cyanoacetaldehyde diethylacetal, 3,3-dimethoxypropanenitrile, or 1,3-dioxolane-2-acetonitrile; and the compound (V) is 3-dimethylamino-2-acrylonitrile or 3-morpholinyl-2-acrylonitrile.

The compound (VI) is a compound from which cyanoacetaldehyde can be prepared, and preferably is

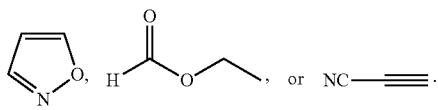

For example:

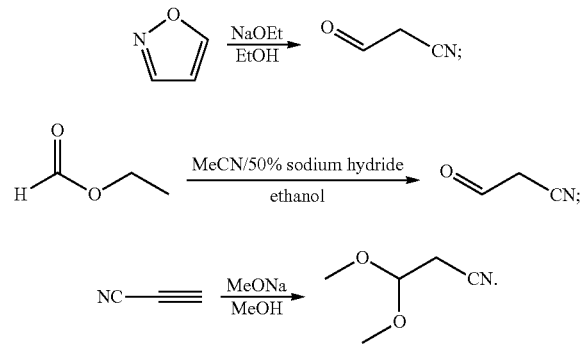

The cyanoacetaldehyde and the compounds (IV), (V) and (VI) are commercially available chemicals, or can be prepared according to literature methods.

The compound of formula (II) can be prepared from the reduction of the compound of formula (III). The reduction reaction may be carried out by catalytic hydrogenation in the presence of hydrogenation catalyst, wherein the hydrogenation catalyst may be selected from the group consisting of Pd/C, Raney-Ni and $PtO_2$, or the reduction reaction may be performed in the presence of suitable reduction agent, such as iron powder, zinc powder or $SnCl_2$. The reaction scheme is illustrated as follows:

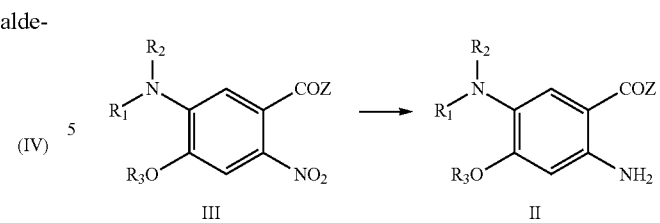

The compound of formula (III) can be prepared by the following processes. (1) In the case of when Z is OR, it can be prepared by nitration of the corresponding substituted benzoate compound (VII), as illustrated in the following reaction scheme:

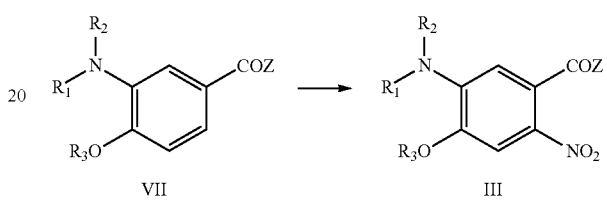

wherein the substituted benzoate compound (VII) can be purchased from the market or prepared according to literature methods, and the specific nitration process may refer to example 1. (2) In the case of when Z is $NH_2$, the compound of formula (III) can be prepared by aminolysis of a compound of formula (III) in which Z is $OCH_3$.

Specifically, the compound of the formula (I) may be prepared through the following several processes.

(1) Compound (IV) or compound (V) is firstly hydrolyzed to produce cyanoacetaldehyde, which then is condensed with the compound of formula (II) or acid addition salt thereof to give the compound of the formula (I). In this process, the hydrolysis is preferably performed under an acidic condition. The acidic condition is preferably in the presence of acid selected from the group consisting of trifluoroacetic acid, hydrochloric acid and sulfuric acid. The condensation is generally carried out at a temperature within the range of −20° C. to the reflux temperature.

(2) Treating compound (IV) or compound (V) with a compound of formula (II) or acid addition salt thereof through one-pot process to give the compound of the formula (I). The reaction may be performed under an acidic condition or neutral condition, wherein the acidic condition is preferably in the presence of acid selected from the group consisting of trifluoroacetic acid, acetic acid and p-toluenesulfonic acid, the reaction temperature is generally in the range of −20° C. to the reflux temperature, and the solvent is preferably selected from acetic acid, ethanol, water, chloroform, chlorobenzene and the mixture thereof.

(3) Condensing directly cyanoacetaldehyde and a compound of formula (II) or an acid addition salt thereof to give the compound of the formula (I).

(4) In a one-pot process, compound (VI) is first treated in an alkaline condition to give cyanoacetaldehyde, which, without separation, is condensed directly with a compound of formula (II) or an acid addition salt thereof to give the compound of the formula (I).

Among the preparation methods for the compound of the formula (I), the methods (1) and (2) are preferred. It is especially preferable that the compound (V) is treated with a compound of formula (II) or an acid addition salt thereof in the presence of glacial acetic acid or p-toluenesulfonic acid to give the compound of the formula (I) with a high yield of 95%. The reaction temperature is within the range of −20° C. to the reflux temperature.

According to still another object of the present invention, provided is the use of the compound of the formula (I), which is characterized in that a compound of formula A is prepared from the compound of the formula (I) by the following methods. The compound of the formula (I) is cyclized in the presence of alkali or alkali metal to give a compound of formula A wherein W=OH, as illustrated in the following reaction scheme:

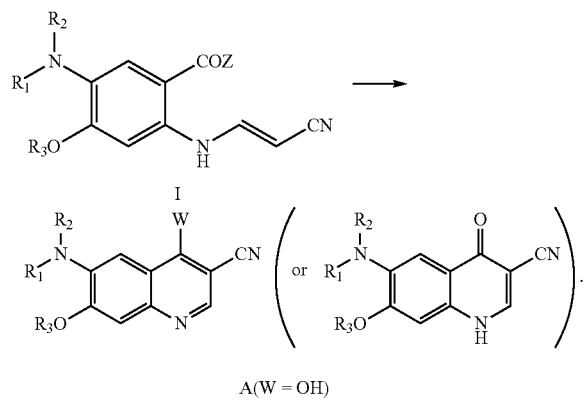

Alternatively, the compound of the formula (I) is cyclized in the presence of alkali or alkali metal, followed by chlorination to give a compound of formula A wherein W=Cl, as illustrated in the following reaction scheme:

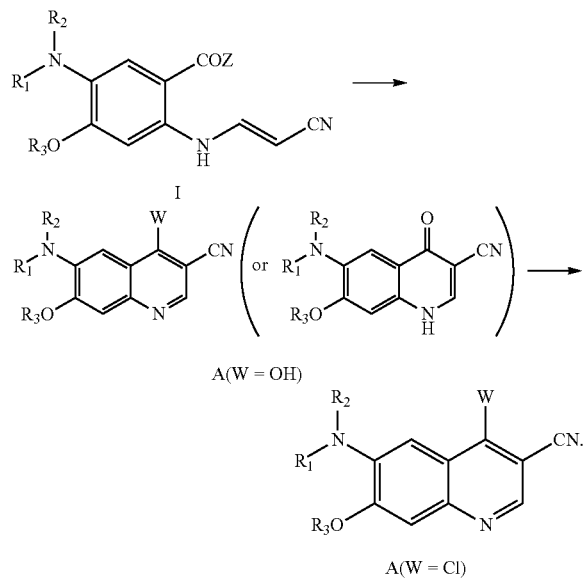

The specific conditions for preparing the compound of formula A (W=OH) from the compound of the formula (I) are as follow: The alkali is selected from the group consisting of an organic base and an inorganic base, such as, 1,8-diazabicyclo[5.4.0]undec-7-ene(DBU), potassium tert-butoxide, NaH, NaOH, KOH, sodium alkoxide, potassium alkoxide, potassium carbonate, pyridine or 4-dimethylaminopyridine (DMAP), but it is not limited thereto, and more preferably sodium alkoxide, NaOH, NaH, DBU, potassium tert-butoxide, or potassium carbonate. The alkali metal includes lithium, sodium, potassium, cesium and the like, and more preferably sodium and potassium. The reaction temperature is within the range of room temperature to the reflux temperature. The solvent includes any solvent or mixture of solvents suitable for this reaction. It is preferably selected from methanol, ethanol, tert-butyl alcohol, acetonitrile, DMF, toluene and chlorobenzene, but it is not limited thereto.

The technical effects and advantages of the present invention are as follows.

(1) Compared with the known literature methods, the method of preparing the compound A from the compound (I) according to the present invention can avoid using the high temperature condition and the high boiling point solvent, and thus is safe and environment-friendly.

(2) The compound (I) can be obtained conveniently from industrial raw materials with high yield.

(3) The reagents and catalysts used in the present invention are commonly conventional industrial raw materials. The use of high toxic solvents is avoided. The raw materials are easily obtained with low cost. The work-up procedure is convenient. The operation is simple. The production cost is low. So, the method is suitable for industry production.

(4) This process possesses mild reaction condition, high total yield and high purity, avoiding the disadvantages of decomposition of the target compounds at a high temperature and the increase of high impurities and low yield in the known methods.

Generally, the present invention has achieved a new synthetic route and method to prepare 6-substituted amino-4-hydroxy-3-cyanoquinoline compounds, which is mild in reaction condition, easy in operation, safe and effective.

BEST MODE FOR CARRYING OUT THE INVENTION

The present invention will be further explained with reference to the following examples, which are merely an illustration of the preferred embodiments of the present invention and not for purpose of limitation. The temperature and reagents employed in the following examples can be substituted with the corresponding temperature and reagents described above to achieve the objects of the present invention.

In the following examples, nuclear magnetic resonance (NMR) spectra were measured on a Bruker AMX-400 nuclear magnetic resonance spectrometer using TMS as an internal standard with the unit of chemical shift of ppm.

Example 1

Methyl 4-ethoxy-5-acetylamido-2-nitrobenzoate (a compound of formula III)

Method 1:
Methyl 3-acetylamido-4-ethoxybenzoate (95.0 g, 0.4 mol), which is commercially available, or may be prepared from a commercial material of methyl 3-amino-4-hydroxybenzoate by the methods disclosed in WO2005034955A1 and WO2006127207, was dissolved in nitromethane (1300 mL) at room temperature, followed by addition of fuming nitric acid (10.0 mL, 0.24 mol). After the mixture was stirred for 1 h at room temperature, another fuming nitric acid (38.0 mL, 0.9 mol) was added and the mixture was stirred for 2 h at 30° C. Then the reaction mixture was poured into an aqueous solution (1200 mL) of sodium carbonate (80.0 g, 0.75 mol), and stirred, followed by addition of dichloromethane (1000 mL). After separated, the organic layer was washed with water, dried, and distilled off the solvent to give 110.5 g of the title compound as a light yellow solid with a yield of 98.0%.

$^1$HNMR (300 MHz, DMSO-d6) δ 1.52 (t, 3H), 2.25 (s, 3H), 3.89 (s, 3H), 4.23 (q, 2H), 7.44 (s, 1H), 7.91 (br, 1H), 8.74 (s, 1H).

MS/ESI: 282.9 (M+H), 305.0 (M+Na), 281.0 (M−H).

Method 2:

Methyl 3-acetylamido-4-ethoxy benzoate (95.0 g, 0.4 mol) was put into a flask, followed by addition of $CH_2Cl_2$ (600 mL). Then fuming $HNO_3$ (1.2-3.2 mol) was added thereinto, and the mixture was reacted for 24-48 h at room temperature. Then the reaction mixture was poured into ice water to generate a precipitate, stirred uniformly and filtered. The filter cake was washed with water, and dried to give the title compound with a yield>90%.

Method 3:

65 wt. % $HNO_3$ (500 mL) was added into methyl 3-acetylamido-4-ethoxybenzoate (95.0 g, 0.4 mol), and reacted for 12-24 h at room temperature. Then the reaction mixture was poured into ice water to generate a precipitate, stirred uniformly and filtered. The filter cake was washed with water, and dried to give the title compound with a yield of 76% and a good purity.

Example 3

Methyl 4-ethoxy-5-acetylamido-2-aminobenzoate (a compound of formula II, R=methyl)

The title compound of example 1 of methyl 4-ethoxy-5-acetylamido-2-nitrobenzoate (320 g, 1.13 mol) and Raney-Ni (40 g) were mixed with THF (1500 mL) and methanol (1500 mL) and stirred for 3 h under hydrogen. The reaction mixture was filtered, washed with dichloromethane, and the filtrate was distilled off the solvent to give 260 g of methyl 4-ethoxy-5-acetylamido-2-aminobenzoate with a yield of 91%.

$^1$HNMR (300 MHz, DMSO-d6) δ 1.45 (t, 3H), 2.16 (s, 3H), 3.82 (s, 3H), 4.06 (q, 2H), 5.71 (br, 1H), 6.04 (s, 1H), 7.26 (s, 1H), 7.35 (br, 1H), 8.68 (s, 1H).

MS/ESI: 252.9 (M+H).

Example 4

Methyl 2-[(2-cyanovinyl)amino]-4-ethoxy-5-acetylamidobenzoate (a compound of formula I, R=methyl)

Trifluoroacetic acid (70 mL) was mixed with water (11 mL, 0.6 mol) at room temperature, and 2-cyanoacetaldehyde diethylacetal (23 mL, 0.15 mol, commercially available) was added thereto. The mixture was reacted for 12 h at room temperature to obtain a solution 1. In addition, the title compound of example 3 (a compound of formula II, i.e. methyl 4-ethoxy-5-acetylamido-2-aminobenzoate) (30 g, 0.12 mol) was suspended in ethyl acetate (400 mL), and the above obtained solution 1 was added thereto. The reaction mixture first turned to clear and then changed to cloudy. After reacted for 3-5 h at room temperature, the reaction was finished. The reaction mixture was filtered, washed with ethyl acetate and dried to give 35 g of the title compound as an offwhite powder with a yield of 96%.

$^1$HNMR (300 MHz, DMSO) δ 1.39 (t, 3H), 2.06 (s, 3H), 3.82 (s, 3H), 4.25 (q, 2H), 5.14 (d, 1H), 7.05 (s, 1H), 8.21 (t, 1H), 8.41 (s, 1H), 9.02 (s, 1H), 10.41 (d, 1H).

MS/ESI: 303.9 (M+H), 326.0 (M+Na), 302.0 (M−H).

Example 5

Methyl 2-[(2-cyanovinyl)amino]-4-ethoxy-5-acetylamidobenzoate (a compound of formula I, R=methyl)

To a mixture of trifluoroacetic acid (90 mL), chloroform (30 mL) and water (30 mL) at room temperature, 2-cyanoacetaldehyde diethylacetal (23 mL, 0.15 mol, commercially available) was added and reacted for 12 h at room temperature to obtain a solution 1. In addition, the title compound of example 3 (a compound of formula II, i.e. methyl 4-ethoxy-5-acetylamido-2-aminobenzoate) (30 g, 0.12 mol) was suspended in ethyl acetate (700 mL), followed by addition of the above obtained solution 1. After reacted for 5 h at room temperature, the reaction was finished. The reaction mixture was filtered, washed with ethyl acetate and dried to give 32 g of the title compound as an offwhite powder with a yield of 86%.

Example 6

Methyl 2-[(2-cyanovinyl)amino]-4-ethoxy-5-acetylamidobenzoate (a compound of formula I, R=methyl)

To a mixture of trifluoroacetic acid (60 mL) and water (10 mL), 2-cyanoacetaldehyde diethylacetal (20 mL, 0.133 mol, commercially available) was added, and reacted for 9 h at room temperature to obtain a solution 1. In addition, the title compound of example 3 (a compound of formula II, i.e. methyl 4-ethoxy-5-acetylamido-2-aminobenzoate) (30 g, 0.12 mol) was suspended in ethyl acetate (700 mL), followed by addition of the above obtained solution 1. After reacted for 5 h at room temperature, the reaction was finished. The reaction mixture was filtered, washed with ethyl acetate and dried to give the title compound as an offwhite powder with a yield of 91%.

Example 7

6-Acetylamido-7-ethoxy-3-cyano-4-hydroxyquinoline (a compound of formula A, W=hydroxy)

The title compound of example 4 (a compound of formula I, Methyl 2-[(2-cyanovinyl)amino]-4-ethoxy-5-acetylamidobenzoate) (30 g, 0.1 mol) and NaOH (8 g, 0.2 mol) were suspended in absolute ethanol (1000 mL) at room temperature, and reacted for 10 h at 60° C. under $N_2$. The reaction mixture was slightly cooled down to 40-50° C., diluted with water (1500 mL), adjusted pH to 3 with 10% HCl solution. The light yellow precipitate was filtered and washed with water and dried to give 21.4 g of the title compound as a gray yellow solid with a yield of 80%. The structure of the product was confirmed by TLC and H-NMR and to be in conformity with the values reported in the literature.

$^1$H NMR (DMSO-$d_6$, δ): 1.45 (t, 3H, J=6.6 Hz), 2.14 (s, 3H), 4.20 (q, 2H, J=6.6 Hz), 7.05 (s, 1H), 8.59 (d, 1H, J=6.3 Hz), 8.70 (s, 1H), 9.18 (s, 1H), 12.52 (d, 1H, J=6.3 Hz);

$^{13}$C NMR (DMSO-$d_6$, δ): 14.13, 23.98, 64.62, 92.97, 99.75, 116.32, 117.04, 118.67, 126.54, 136.55, 145.42, 152.86, 168.68, 173.49;

ESI-MS (m/z) 270 (M−H).

Example 8

6-Acetylamido-7-ethoxy-3-cyano-4-hydroxyquinoline (a compound of formula A, W=hydroxy)

The title compound of example 4 (a compound of formula I, Methyl 2-[(2-cyanovinyl)amino]-4-ethoxy-5-acetylamidobenzoate) (30 g, 0.1 mol) and sodium ethoxide (0.2 mol) were added to absolute ethanol (1000 mL) at room temperature, and was stirred under refluxing for 2-3 h. The reaction mixture was slightly cooled down to 40-50° C., condensed to 300 mL, diluted with water (600 mL), adjusted pH to 3 to generate a light yellow precipitate. The precipitate was filtered and washed with water and dried to give 22.7 g of the title compound as a gray yellow solid with a yield of 85%.

Example 9

6-Acetylamido-7-ethoxy-3-cyano-4-hydroxyquinoline (a compound of formula A, W=hydroxy)

The title compound of example 4 (a compound of formula I, methyl 2-[(2-cyanovinyl)amino]-4-ethoxy-5-acetylamidobenzoate) (15 g, 0.05 mol) was suspended in acetonitrile (300 mL, dried by $P_2O_5$), followed by addition of DBU (15 mL, 0.1 mol). The mixture was stirred under refluxing for 14-20 h under $N_2$. The work-up procedure is similar to that of example 7 with a yield of 85%.

Example 10

6-Acetylamido-7-ethoxy-3-cyano-4-hydroxyquinoline (a compound of formula A, W=hydroxy)

The title compound of example 4 (a compound of formula I, methyl 2-[(2-cyanovinyl)amino]-4-ethoxy-5-acetylamidobenzoate) (15 g, 0.05 mol), $K_2CO_3$ (0.1 mol) and DMF (100 mL) were mixed, and stirred for 12 h at 100° C. under $N_2$ to complete the reaction. The work-up procedure is similar to that of example 7 with a yield of 80%.

Example 11

6-Acetylamido-7-ethoxy-3-cyano-4-hydroxyquinoline (a compound of formula A, W=hydroxy)

The title compound of example 4 (a compound of formula I, methyl 2-[(2-cyanovinyl)amino]-4-ethoxy-5-acetylamidobenzoate) (15 g, 0.05 mol) was suspended in acetonitrile (300 mL, dried over $P_2O_5$), followed by addition of NaOH (0.1 mol). The mixture was stirred under refluxing for 8 h under $N_2$. The work-up procedure is similar to that of example 7 with a yield of 89%.

Example 12

6-Acetylamido-7-ethoxy-3-cyano-4-hydroxyquinoline (a compound of formula A, W=hydroxy)

The title compound of example 4 (a compound of formula I, methyl 2-[(2-cyanovinyl)amino]-4-ethoxy-5-acetylamidobenzoate) (30 g, 0.1 mol), $K_2CO_3$ (0.25 mol) and absolute ethanol (1000 mL) were mixed, and stirred under refluxing for 18 h. The work-up procedure is similar to that of example 7 with a yield of 87%.

Example 13

6-Acetylamido-7-ethoxy-3-cyano-4-hydroxyquinoline (a compound of formula A, W=hydroxy)

The title compound of example 4 (a compound of formula I, methyl 2-[(2-cyanovinyl)amino]-4-ethoxy-5-acetylamidobenzoate) (15 g, 0.05 mol) was suspended in absolute ethanol (300 mL), followed by addition of NaOH (0.1 mol). The mixture was stirred under refluxing for 2 h under $N_2$. The work-up procedure is similar to that of example 7 with a yield of 88%.

Example 14

6-Acetylamido-7-ethoxy-3-cyano-4-hydroxyquinoline (a compound of formula A, W=hydroxy)

The title compound of example 4 (a compound of formula I, methyl 2-[(2-cyanovinyl)amino]-4-ethoxy-5-acetylamidobenzoate) (15 g, 0.05 mol) was suspended in absolute ethanol (300 mL), followed by addition of NaOH (0.1 mol). The mixture was stirred under refluxing for 10 h at 60° C. under $N_2$. The work-up procedure is similar to that of example 7 with a yield of 85%.

Example 15

Ethyl 4-ethoxy-5-acetylamido-2-aminobenzoate (a compound of formula II, R=ethyl)

The title compound was prepared from ethyl 3-acetylamido-4-ethoxybenzoate using a procedure similar to that described in example 1 and 3.
$^1$H NMR (300 MHz, DMSO): δ 1.27 (t, 3H), 1.36 (t, 3H), 1.99 (s, 3H), 4.02 (q, 2H), 4.19 (q, 2H), 6.34 (s, 1H), 6.59 (s, 2H), 7.97 (s, 1H), 8.78 (s, 1H).
MS/ESI: 289.2 (M+Na).

Example 16

Ethyl 2-[(2-cyanovinyl)amino]-4-ethoxy-5-acetylamidobenzoate (a compound of formula I, R=ethyl)

To a mixture of trifluoroacetic acid (60 mL) and water (10 mL) at room temperature, 2-cyanoacetaldehyde diethylacetal (20 mL, 0.133 mol, commercially available) was added, and reacted for 9 h at room temperature to obtain a solution 1. In addition, the title compound of example 15 (26 g, 0.1 mol) was suspended in ethyl acetate (400 mL) at room temperature, followed by addition of the above obtained solution 1. The reaction mixture first became clear and then changed to cloudy. After stirring for 12 h at room temperature, the reaction mixture was filtered and washed with ethyl acetate and dried to give 28 g of the title compound as a gray white powder with a yield of 90.6%.
$^1$HNMR (300 MHz, DMSO) δ 1.30 (t, 3H), 1.39 (t, 3H), 2.06 (s, 3H), 4.22 (q, 2H), 4.29 (q, 2H), 5.13 (d, 1H), 7.04 (s, 1H), 8.20 (t, 1H), 8.36 (s, 1H), 9.01 (s, 1H), 10.45 (d, 1H).
MS/ESI: 316.0 (M−H).

Example 17

6-acetylamido-7-ethoxy-3-cyano-4-hydroxyquinoline (a compound of formula A, W=hydroxy)

The title compound of example 16 (15 g, 47 mmol) and NaOH (4 g, 0.1 mol) were suspended in absolute ethanol (1000 mL), and refluxed for 1 h under $N_2$. The reaction mixture was slightly cooled down to 40-50° C., diluted with water (1500 mL), adjusted pH to 3 with a 10% HCl solution to precipitate a white solid. The precipitate was filtered and washed with water and dried to give the title compound as a light yellow solid with a yield>70%.

Example 18

Ethyl 2-[(2-cyanovinyl)amino]-4-ethoxy-5-acetylamidobenzoate (a compound of formula I, R=ethyl)

To a mixture of trifluoroacetic acid (60 mL) and water (10 mL) at room temperature, 1,3-dioxolane-2-acetonitrile (0.13 mol) (commercially available, or prepared according to the method disclosed in JP06087781A) was added and stirred for 9 h at room temperature to obtain a solution 1. In addition, the title compound of example 15 (26 g, 0.1 mol) was suspended in ethyl acetate (400 mL), followed by addition of the above obtained solution 1. The reaction mixture was stirred for 12 h at room temperature. It was then filtered and washed with ethyl acetate and dried to give 27 g of the title compound as a gray white powder with a yield of 87%.

Example 19

Ethyl 2-[(2-cyanovinyl)amino]-4-ethoxy-5-acetylamidobenzoate (a compound of formula I, R=ethyl)

The title compound of example 15 (26 g, 0.1 mol) was added to 1,2-dimethoxyethane (400 mL) at room temperature, followed by addition of 3-dimethylamino-2-acrylonitrile (commercially available, or prepared according to the method disclosed in Synthesis, 1986, 5, 419-20) (0.13 mol). The mixture was stirred for 12 h at room temperature to complete the reaction. It was then filtered and washed with ethyl acetate and dried to give 27.5 g of the title compound as a gray white powder with a yield of 89%.

Example 20

6-Acetylamido-7-ethoxy-3-cyano-4-hydroxyquinoline (a compound of formula A, W=hydroxy)

The title compound of example 19 (0.1 mol) and sodium ethoxide (0.2 mol) were suspended in absolute ethanol (1000 mL) at room temperature, and stirred for 10 h at 60° C. under $N_2$. The reaction mixture was slightly cooled down to 40-50° C., diluted with water (1500 mL), adjusted pH to 3 with 10% HCl solution to precipitate a light yellow solid. The precipitate was filtered and washed with water and dried to give the title compound as a gray yellow solid with a yield>80%.

Example 21

6-Acetylamido-7-ethoxy-3-cyano-4-chloro-quinoline (a compound of formula A, W=Cl)

To a solution of the title compound of example 20 (0.1 mol) in diethylene glycol dimethyl ether, $POCl_3$ (22 mL) was added, and stirred at 80° C. (exterior temperature) for 4-4.5 h. The reaction mixture was slowly poured into two volumes of ice-water and stirred for 1 h to precipitate a yellow powder. The precipitate was filtered and washed with water, and then washed with a small amount of diethylene glycol dimethyl ether, and dried at 40° C. to give the title compound A (W=Cl) as a yellow powder with a yield of 69%.

$^1$H NMR (DMSO-$d_6$, δ): 1.50 (t, 3H, J=6.3 Hz), 2.25 (s, 3H), 4.40 (q, 2H, J=6.3 Hz), 7.60 (s, 1H), 9.01 (s, 1H), 9.17 (s, 1H), 9.54 (s, 1H).

ESI-MS (m/z) 290 (M+H).

Example 22

Methyl 2-[(2-cyanovinyl)amino]-4-ethoxy-5-acetylamidobenzoate (a compound of formula I, R=methyl)

The title compound of example 3 (26 g, 0.1 mol) was added to acetic acid (400 mL), followed by addition of 3-dimethylamino-2-acrylonitrile (commercially available, or prepared according to the method disclosed in Synthesis, 1986, 5, 419-20) (0.13 mol). The reaction mixture was stirred for 12 h at room temperature. It was then filtered and washed with ethyl acetate and dried to give 25.3 g of the title compound as a gray white powder with a yield of 81%.

Example 23

Ethyl 2-[(2-cyanovinyl)amino]-4-ethoxy-5-acetylamidobenzoate (a compound of formula I, R=ethyl)

The title compound of example 15 (26 g, 0.1 mol) was suspended in ethyl acetate (400 mL) at room temperature, followed by addition of cyanoacetaldehyde (0.13 mol). The reaction mixture first became clear and then changed to cloudy. It was then stirred for 12 h at room temperature. The precipitate was filtered and washed with ethyl acetate and dried to give 28.5 g of the title compound as a gray white powder with a yield of 92%.

Example 24

Methyl 2-[(2-cyanovinyl)amino]-4-ethoxy-5-acetylamidobenzoate (a compound of formula I, R=methyl)

The title compound of example 3 (30 g, 0.12 mol) was suspended in ethyl acetate (400 mL) at room temperature, followed by addition of cyanoacetaldehyde (0.15 mol). The reaction mixture first became clear and then changed to cloudy. It was stirred for 12 h and then filtered, washed with ethyl acetate and dried to give the title compound as a gray white powder with a yield>90%.

Example 25

Methyl 2-[(2-cyanovinyl)amino]-4-ethoxy-5-acetylamidobenzoate (a compound of formula I, R=methyl)

The title compound of example 3 (30 g, 0.12 mol) was suspended in ethyl acetate (400 mL) at room temperature, followed by addition of 2-cyanoacetaldehyde diethylacetal (23 mL, 0.15 mol, commercially available), trifluoroacetic acid (70 mL) and water (11 mL, 0.6 mol). The reaction mixture was stirred for 10-12 h at room temperature to complete the reaction. It was then filtered under suction, washed with ethyl acetate and dried to give the title compound as an off-white powder with a yield>90%.

Example 26

6-Acetylamido-7-ethoxy-3-cyano-4-chloro-quinoline (a compound of formula A, W=Cl)

The title compound of example 4 (a compound of formula I, methyl 2-[(2-cyanovinyl)amino]-4-ethoxy-5-acetylamidobenzoate) (30 g, 0.1 mol), $K_2CO_3$ (0.25 mol) and absolute ethanol (1000 mL) were mixed and refluxed for 10 h. The work-up procedure is similar to that of example 7. The obtained product was dissolved in 1,2-dimethoxyethane, followed by addition of phosphorus oxychloride (22 mL). The reaction mixture was stirred at 80° C. (exterior temperature) for 4-4.5 h. The mixture was then slowly poured into two volumes of ice-water and stirred for 1 h to precipitate a yellow powder. The precipitate was filtered and washed with water, and then washed with a small amount of 1,2-dimethoxyethane, and dried at 40° C. to give the title compound A (W=Cl) as a yellow powder.

Example 27

Methyl 2-[(2-cyanovinyl)amino]-4-ethoxy-5-acetylamidobenzoate (a compound of formula I, R=methyl)

The title compound of example 3 (1 kg, 4 mol) was added into glacial acetic acid (9000 mL), and stirred at room temperature until it was fully dissolved. Then 3-dimethylamino-2-acrylonitrile (600 mL, 6 mol) was added thereinto and stirred at 25-30° C. A large amount of gray yellow solid was generated gradually, and the mixture was stirred continually for 1-2 h. The reaction process was monitored by TLC. When finished, the reaction mixture was diluted with 5OL water, filtered, and dried to give 1.14 kg of the title compound with a yield of 94.8%.

Example 28

6-Acetylamido-7-ethoxy-3-cyano-4-hydroxyquinoline (a compound of formula A, W=hydroxy)

Metal sodium (10.6 g, 0.461 mol) was added to absolute ethanol (1500 mL) and stirred to entire dissolution. The title compound of example 27 (100 g, 0.354 mol) was added thereinto and reacted at 75° C. The reaction mixture became clear rapidly. The reaction was finished after 1.5 h by TLC monitored. After cooled down to about 50° C. by nature, the reaction mixture was diluted with 3000 mL of water, adjusted pH to 6-7 with a 2M HCl solution to precipitate a large amount of solid. The precipitate was filtered and dried to give 88 g of the title compound as a yellowish-brown solid with a yield of 91.6%.

Example 29

6-Acetylamido-7-ethoxy-3-cyano-4-chloro-quinoline (a compound of formula A, W=Cl)

The title compound of example 28 (23 g, 0.0857 mol) was added to diethylene glycol dimethyl ether (400 mL), and then $POCl_3$ (24 mL, 0.257 mol) was added thereto and stirred at 85° C. for 4-4.5 h. The reaction mixture was slowly poured into two volumes of ice-water and stirred for 1 h to precipitate a yellow powder. The precipitate was filtered and washed with water and then washed with a small amount of diethylene glycol dimethyl ether, and dried at 40° C. to give 23 g of the title compound with a yield of 93.6%.

Example 30

Methyl 2-[(2-cyanovinyl)amino]-4-ethoxy-5-acetylamidobenzoate (a compound of formula I, R=methyl)

The title compound of example 3 (2 g, 0.00793 mol) was mixed with chlorobenzene (40 mL) and p-TsOH.$H_2$O (300 mg) and stirred at room temperature, and 3-dimethylamino-2-acrylonitrile (600 mL, 6 mol) was added thereinto. TLC showed that there was a product generated. Additional 0.8 eq. of p-TsOH.$H_2$O was put thereinto after 1 h, and there was a significant increase of product. After the reaction finished, the reaction mixture was filtered and dried to give 1.73 g of the title compound with a yield of 72%.

Example 31

Methyl 2-[(2-cyanovinyl)amino]-4-ethoxy-5-acetylamidobenzoate (a compound of formula I, R=methyl)

The title compound of example 3 (2 g, 0.00793 mol) was mixed with absolute ethanol (40 mL) and p-TsOH.$H_2$O (750 mg) and stirred at room temperature to dissolution. Then 3-dimethylamino-2-acrylonitrile (1.1 mL, 0.011 mol) was added thereinto. A solid was formed after 30 min. Additional p-TsOH.$H_2$O (850 mg) was put thereinto after 1.5 hours. The reaction was continued and monitored by TLC. After the reaction was finished, the reaction mixture was filtered to obtain 1.68 g of solid with a good purity and a yield of 70%.

Example 32

6-Acetylamido-7-ethoxy-3-cyano-4-hydroxyquinoline (a compound of formula A, W=hydroxy)

60% NaH (28 mg, 0.0007 mol) was added to DMF (1.5 mL) and stirred for 10 min at room temperature. The title compound of example 27 (0.1 g, 0.00033 mol) was added thereinto and stirred at 90° C. The reaction mixture was dissolved rapidly to be clear with a brown color. The reaction was substantially completed after 30 min. The reaction mixture was diluted with 3 mL of water, adjusted pH to 3-4 with a 2M HCl solution, and filtered to obtain the title compound as a reddish-brown solid.

Example 33

6-Acetylamido-7-ethoxy-3-cyano-4-hydroxyquinoline (a compound of formula A, W=hydroxy)

60% NaH (28 mg, 0.0007 mol) was added to chlorobenzene (2 mL), and DMF (0.2 mL) was added thereinto, and stirred for 10 min at room temperature. The title compound of example 27 (0.1 g, 0.00033 mol) was added thereinto, and stirred at 100° C. for 1-2 h. The reaction mixture was diluted with 3 mL of water, adjusted pH to 3-4 with a 2M HCl solution, and filtered to obtain the title compound as a reddish-brown solid Example 34

6-Acetylamido-7-ethoxy-3-cyano-4-hydroxyquinoline (a compound of formula A, W=hydroxy)

60% NaH (28 mg, 0.0007 mol) was mixed with toluene (2 mL) and DMF (0.2 mL), and stirred for 10 min at room temperature. The title compound of example 27 (0.1 g, 0.00033 mol) was added thereto, and stirred at 100° C. for 1-2 h. The reaction mixture was diluted with 3 mL of water, adjusted pH to 3-4 with a 2M HCl solution, filtered to obtain the title compound as a reddish-brown solid.

Example 35

6-Acetylamido-7-ethoxy-3-cyano-4-hydroxyquinoline (a compound of formula A, W=hydroxy)

The title compound of example 27 (0.1 g, 0.00033 mol) was mixed with acetonitrile (3 mL) and DBU (0.1 mL, 2 eq), and refluxed. The reaction mixture was dissolved rapidly to be clear. The reaction was monitored by TLC, and the work-up procedure is similar to that of example 28 to obtain the title compound with a yield of 60%.

Example 36

Methyl 2-[(2-cyanovinyl)amino]-4-ethoxy-5-acetylamidobenzoate (a compound of formula I, R=methyl)

The title compound of example 3 (2.9 g, 0.01 mol) was dissolved in methanol (20 mL), and 36% concentrated HCl (0.84 mL) was dropped thereinto. After stirred for 10 min at room temperature, the reaction mixture was condensed to dryness to give a hydrochloride salt of the compound. The obtained hydrochloride salt compound was added to glacial acetic acid (25 mL), and stirred to complete dissolution at room temperature. 3-Dimethylamino-2-acrylonitrile (1.5 mL, 0.015 mol) was added thereinto, and a solid product was precipitated gradually. The reaction continued for 1 hour. After there was no starting material existing, the reaction mixture was filtered and dried to obtain 2.7 g of the title compound as a light yellow solid with a yield of 90%.

Example 38

Methyl 2-[(2-cyanovinyl)amino]-4-ethoxy-5-acetylamidobenzoate (a compound of formula I, R=methyl)

The hydrochloride salt of the title compound of example 3 (2.9 g, 0.01 mol) was added to glacial acetic acid (25 mL), and stirred to dissolve completely at room temperature. 3-Morpholinyl-2-acrylonitrile (2.1 g, 0.015 mol, commercially available) was added thereinto. A solid product was precipitated after 20 min. The reaction continued for 1 hour. After there was no starting material existing, the reaction mixture was filtered and dried to give 2.8 g of the title compound as a light yellow solid with a yield of 92.4%.

Example 39

6-Acetylamido-7-ethoxy-3-cyano-4-hydroxyquinoline (a compound of formula A, W=hydroxy)

The title compound of example 27 (3.03 g, 0.01 mol) was added to tert-butanol (30 mL), followed by addition of potassium tert-butoxide (1.44 g, 0.015 mol). The mixture was heated to 80° C. and stirred for 2 h. After there was no starting material existing, the tert-butanol was distilled off, and water (30 mL) was added. The reaction mixture was adjusted to pH=3-4 with a 4M HCl solution to precipitate a solid. The precipitate was filtered and dried to give 2.4 g of the title compound with a yield of 88.6%.

Example 40

Phenyl 4-ethoxy-5-acetylamido-2-aminobenzoate (a compound of formula I, R=phenyl)

Phenyl 3-acetylamido-4-ethoxybenzoate (commercially available) (5.0 g, 16.7 mmol) was dissolved in dichloromethane (40 mL), and 95% fuming nitric acid (2.8 mL, 63.3 mmol) was added thereinto. The mixture was stirred for 2 h at 25° C. Then it was sequentially washed with water and a sodium bicarbonate aqueous solution, dried, and distilled off the solvent. The obtained brown solid was dissolved in methanol (75 mL), and Raney-Ni was added thereinto. Hydrogen gas was introduced to carry out a hydrogenation under normal pressure at room temperature until no hydrogen gas was absorbed. The mixture was filtered. The filtrate was distilled off to obtain 4.43 g of the title compound with a total yield for the two steps of 84%.

$^1$H NMR (DMSO-d6): δ 8.85 (1H, s), 8.23 (1H, s), 7.44 (2H, t), 7.21 (1H, t), 7.18 (2H, d), 6.68 (2H, s), 6.41 (1H, s), 4.07 (2H, q), 2.01 (3H, s), 1.38 (3H, t).

Example 41

Phenyl 2-[(2-cyanovinyl)amino]-4-ethoxy-5-acetylamidobenzoate (a compound of formula I, R=phenyl)

The title compound of example 40 (3.14 g, 0.01 mol) was added to glacial acetic acid (25 mL), and stirred to dissolve completely at room temperature. 3-Morpholinyl-2-acrylonitrile (2.1 mL, 0.015 mol, commercially available) was added thereto, and stirred for 1.5 h. After there was no starting material existing, the reaction mixture was filtered and dried to obtain 3.29 g of the title compound as a light yellow solid with a yield of 90.1%.

$^1$H NMR (DMSO-d6): δ 10.64 (0.7H, d), 10.30 (0.3H, d), 8.71 (0.7H, s), 8.66 (0.3H, s), 8.24 (0.3H, t), 8.08 (0.7H, dd), 7.53-7.23 (5H, m), 7.12 (0.3H, s), 7.10 (0.7H, s), 5.17 (0.3H, d), 4.66 (0.7H, d), 4.28 (2H, q), 2.09 (3H, s), 1.42 (3H, t).

Example 42

6-Acetylamido-7-ethoxy-3-cyano-4-hydroxyquinoline (a compound of formula A, W=hydroxy)

60% NaH (82 mg, 2.05 mmol) was added to DMSO (2.5 mL) under ice-bath, and stirred for 5 min at room temperature. The title compound of example 41 (0.5 g, 1.37 mmol) was added in batches thereinto, and stirred for 2 h at room temperature. After there was no starting material existing, the reaction mixture was poured into 10 mL of water, adjusted pH to 3-4 with a 4M HCl solution, and filtered to give a light yellow solid, which was dried to obtain 0.35 g of the title compound with a yield of 94.3%.

Example 43

4-Ethoxy-5-acetylamido-2-nitro-benzoylamide (a compound of formula III)

The title compound of example 1 (0.5 g, 1.77 mmol) was added to an one-necked flask, followed by addition of 15 mL of ammonia water. After stirred over night at room temperature, the reaction was complete as identified by TLC. The reaction mixture was filtered, washed with water, and dried to give a light yellow solid with a yield of 90%.

$^1$H NMR (DMSO-d6, 300 MHz): δ 1.39 (t, 3H), 2.16 (s, 3H), 4.2 (m, 2H), 7.5 (s, 1H), 7.6 (s, 1H), 7.9 (s, 1H), 8.3 (s, 1H), 9.4 (s, 1H).

MS (ESI) m/z: 268.2 (M+1), 290.1 (M+23).

Example 44

Methyl 4-ethoxy-5-acetylamido-2-amino benzoylamide (a compound of formula II, Z=amino)

The title compound of example 43 (4.7 g, 0.0177 mol), Fe (5.952 g, 0.106 mmol, 6 eq.), NH$_4$Cl (0.95 g, 0.0177 mol, 1 eq.) and 95% ethanol (150 mL) were added to a 500 mL one-necked flask, and stirred at 75° C. 2M HCl solution (5 mL) was added into the flask after 1 h. Another 1 h later, TLC showed that the reaction was complete. The reaction mixture was filtered. The filtrate was condensed to remove most of ethanol, and poured into ice water to precipitate a large amount of solid. The precipitate was filtered and dried to give 1.848 g of the title compound solid with a yield of 52%.

$^1$H NMR (DMSO-d6, 300 MHz) δ 1.3 (t, 3H), 2.0 (s, 3H), 4.0 (m, 2H), 6.3 (s, 1H), 6.6 (s, 1H), 7.6 (s, 1H), 8.3 (s, 1H), 8.8 (s, 1H).

MS (ESI) m/z: 260.2 (M+23), 236.4 (M−1).

Example 45

2-[(2-Cyanovinyl)amino]-4-ethoxy-5-acetylamido benzoylamide (a compound of formula I, Z=amino)

To a solvent mixture of $CF_3COOH$ (1 mL), $CHCl_3$ (0.3 mL) and $H_2O$ (0.3 mL), 2-cyanoacetaldehyde diethylacetal (126 μL, 0.842 mmol, 2 eq.) was added, and stirred over night at room temperature.

The title compound of example 44 (100 mg, 0.421 mmol) was added to a 10 mL one-necked flask, and then 3 mL ethyl acetate was added thereto and stirred to be a suspension. The above freshly prepared cyanoacetaldehyde was added thereto, and the mixture became a clear yellowish brown solution immediately. After the reaction was substantially completed as identified by TLC, the reaction mixture was filtered and dried to give 82 mg of solid with a yield of 68%.

$^1$H NMR (DMSO-d6, 300 MHz) δ 1.4 (t, 3H), 2.1 (s, 3H), 4.2 (m, 2H), 5.3 (d, 1H), 7.1 (s, 1H), 7.3 (d, 1H), 7.7 (s, 1H), 8.2 (s, 1H), 8.6 (d, 1H), 9.2 (s, 1H), 12.8 (d, 1H).

MS (ESI) m/z: 289.4 (M+1).

Example 46

6-Acetylamido-7-ethoxy-3-cyano-4-hydroxyquinoline (a compound of formula A, W=hydroxy)

Na (8 mg, 0.378 mmol, 1.5 eq) was dissolved in 2 mL of ethanol, and then the title compound of example 45 (70 mg, 0.243 mmol) was added thereto and stirred at 70° C. for 1 h. The reaction mixture was added with a small amount of water, adjusted pH to 3 with a 2M HCl solution to precipitate a solid. The precipitate was filtered and dried to give the title compound as a yellowish brown solid.

The invention claimed is:

1. A compound of the following formula (I),

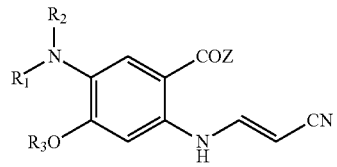

Wherein, Z is OR or $NH_2$;
R is hydrogen, C1-C10 linear or branched alkyl, C2-C5 alkenyl, aryl, or C1-C5 alkyl substituted with aryl;
$R_1$ and $R_2$ are each independently hydrogen, formyl, C1-C10 alkyl, C2-C10 alkenyl, aryl, C1-C10 alkyl substituted with aryl, C1-C10 alkylcarbonyl, arylcarbonyl, C1-C10 alkylcarbonyl substituted with aryl, C1-C10 alkoxycarbonyl, or C1-C10 alkoxycarbonyl substituted with aryl; and $R_3$ is C1-C10 alkyl, C2-C10 alkenyl or aryl, wherein the alkyl is optionally substituted with halogen, alkoxy, aryl, or a heterocyclic group having 1-2 heteroatoms selected from the group consisting of O and N, wherein the heterocyclic group is optionally substituted with C1-C10 alkyl or C1-C10 alkoxy;
wherein the aryl is phenyl or an aromatic heterocyclic group.

2. The compound of formula (I) as set forth in claim 1, wherein,
Z is OR;
R is C1-C4 linear or branched alkyl, benzyl or phenyl;
$R_1$ is hydrogen, formyl, C1-C4 alkylcarbonyl or C1-C4 alkyl;
$R_2$ is hydrogen, formyl, C1-C4 alkylcarbonyl or C1-C4 alkyl; and
$R_3$ is C1-C5 alkyl, phenyl,

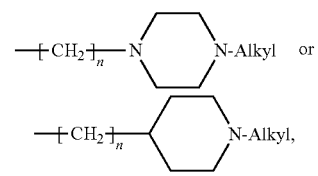

in which n is an integer from 1 to 5, Alkyl is a C1-C5 alkyl.

3. The compound of formula (I) as set forth in claim 2, wherein,
Z is OR;
R is methyl, ethyl or phenyl;
$R_1$ is hydrogen, formyl, acetyl, methyl or ethyl;
$R_2$ is hydrogen, formyl acetyl, methyl or ethyl; and
$R_3$ is methyl, ethyl,

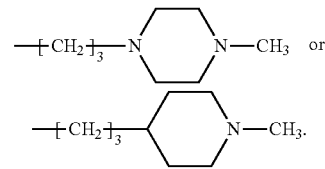

4. The compound of formula (I) as set forth in claim 1, wherein, the compound is one selected from the group consisting of:
methyl 2-[(2-cyanovinyl)amino]-4-ethoxy-5-acetylamidobenzoae;
ethyl 2-[(2-cyanovinyl)amino]-4-ethoxy-5-acetylamidobenzoate; and
phenyl 2-[(2-cyanovinyl)amino]-4-ethoxy-5-acetylamidobenzoate.

5. A method for producing the compound of formula (I) as set forth in claim 1, comprising the step of:
Condensing the compound of the formula (II) or acid addition salt thereof with cyanoacetaldehyde to give the compound of the formula (I);
or, treating the compound of the formula (II) or acid addition salt thereof with the compound of the formula (IV) or (V) to give the compound of the formula (I);
or, in a one-pot process, treating compound (VI) in a certain reaction condition or in the presence of catalyst to give cyanoacetaldehyde, which, without separation, is condensed directly with the compound of the formula (II) or acid addition salt thereof to give the compound of the formula (I);

wherein, the reaction scheme is as follows:

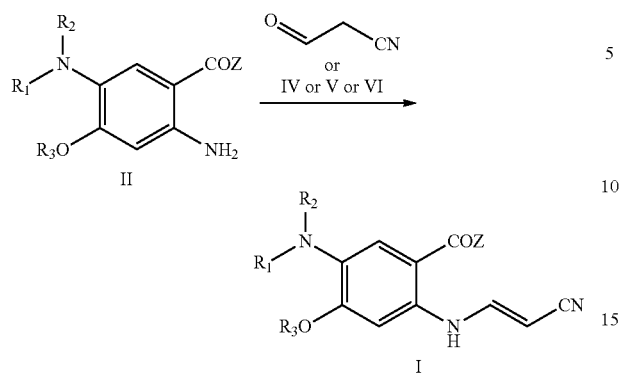

wherein, Z, $R_1$, $R_2$ and $R_3$ are defined the same as the cited claims,
the structures of the compound (IV) and (V) are as follows:

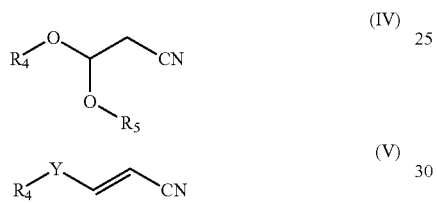

wherein, Y is O or N—$R_5$; $R_4$ and $R_5$ are each independently hydrogen or C1-C5 alkyl, or $R_4$ and $R_5$ may together form a 5-7 membered ring which may contain one or more hetero atoms selected from the group consisting of O, N and S;
the compound (VI) is

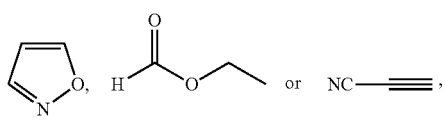

the acid addition salt of the compound of the formula (II) is an inorganic acid salt or an organic acid salt thereof.

6. The method as set forth in claim 5, comprising the step of:
(1) hydrolyzing the compound (IV) or compound (V) to give cyanoacetaldehyde, which then is condensed with the compound of formula (II) or acid addition salt thereof to give the compound of the formula (I); or
(2) treating compound (IV) or compound (V) with the compound of formula (II) or acid addition salt thereof through one-pot process to give the compound of the formula (I); or
(3) condensing directly cyanoacetaldehyde and the compound of formula (II) or acid addition salt thereof to give the compound of the formula (I); or
(4) in a one-pot process, firstly treating compound (VI) in an alkaline condition to give cyanoacetaldehyde, which, without separation, is condensed directly with the compound of formula (II) or acid addition salt thereof to give the compound of the formula (I).

7. The method as set forth in claim 6, wherein,
compound (IV) or compound (V) is firstly hydrolyzed under an acidic condition to produce cyanoacetaldehyde, which then is condensed with the compound of formula (II) or acid addition salt thereof to give the compound of the formula (I), wherein the acidic condition is in the presence of an acid selected from the group consisting of trifluoroacetic acid, hydrochloric acid and sulfuric acid, and the temperature of the condensation reaction is within the range of −20° C. to the refluxing temperature; or
the compound of the formula (I) is prepared through one-pot process by mixing the compound (IV) or compound (V) with the compound of formula (II) or acid addition salt thereof under an acidic or neutral condition, wherein the acidic condition is in the presence of an acid selected from the group consisting of trifluoroacetic acid, acetic acid and p-toluenesulfonic acid, the temperature of the reaction is within the range of −20° C. to the reflux temperature, and the solvent is selected from the group consisting of acetic acid, ethanol, water, chloroform, chlorobenzene and a mixture thereof.

8. The method as set forth in claim 5, wherein,
the compound (IV) is 2-cyanoacetaldehyde diethylacetal, 3,3-dimethoxypropanenitrile, 1,3-dioxolane-2-acetonitrile, and
the compound (V) is 3-dimethylamino-2-acrylonitrile or 3-morpholinyl-2-acrylonitrile.

9. The method as set forth in claim 5, comprising the step of:
treating the compound of formula (II) or acid addition salt thereof with compound (V) under an acidic condition in the presence of glacial acetic acid or p-toluenesulfonic acid to give the compound of the formula (I).

10. The method as set forth in claim 5, wherein,
the compound of formula (II) is prepared from the compound of formula (III) via a reduction reaction:

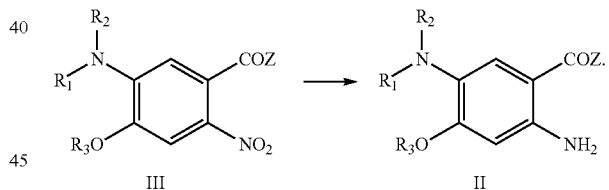

11. The method as set forth in claim 10, wherein,
the reduction reaction is performed by catalytic hydrogenation, wherein the hydrogenation catalyst is selected from the group consisting of Pd/C, Raney-Ni and $PtO_2$, or the reduction reaction is carried out by the addition of reduction agent selected from the group consisting of iron powder, zinc powder or $SnCl_2$.

12. The method as set forth in claim 10, wherein,
the compound of formula (III), in which Z is OR, is prepared by nitration of the following substituted benzoate compound:

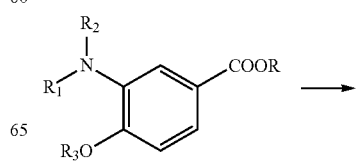

-continued

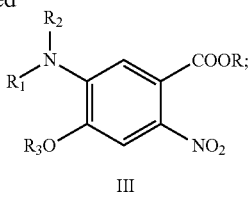

III and the compound of formula (III), in which Z is NH$_2$, is prepared by aminolysis of a compound of formula (III) in which Z is OCH$_3$.

13. A method for producing the compound of formula A from the compound of formula (I) as set forth in claim 1, comprising the step of:

cyclizing the compound of the formula (I) in the presence of alkali or alkali metal to give the compound of formula A in which W is OH, as shown in the following reaction scheme:

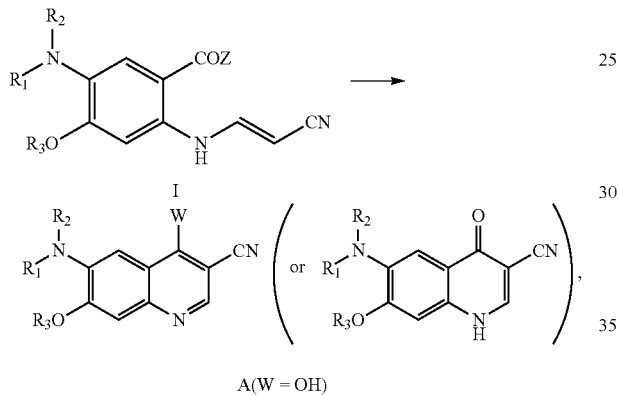

or, cyclizing the compound of the formula (I) in the presence of alkali or alkali metal, followed by chlorination to give the compound of formula A in which W is Cl, as shown in the following reaction scheme:

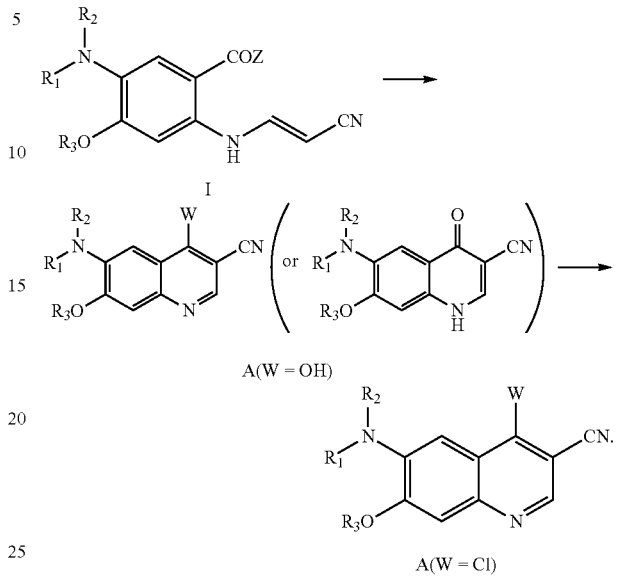

14. The method as set forth in claim 13, wherein, the alkali is selected from the group consisting of 1,8-diazabicyclo[5.4.0]undec-7-ene, potassium tert-butoxide, NaH, NaOH, KOH, sodium alkoxide, potassium alkoxide, potassium carbonate, pyridine and 4-dimethylaminopyridine; the alkali metal is selected from the group consisting of sodium and potassium; the temperature of the reaction is within the range of room temperature to the reflux temperature; and the used solvent is a solvent selected from the group consisting of methanol, ethanol, tert-butyl alcohol, acetonitrile, DMF, toluene and chlorobenzene.

* * * * *